(12) United States Patent
Shapiro

(10) Patent No.: US 6,595,949 B1
(45) Date of Patent: Jul. 22, 2003

(54) AUTOMATIC MUCUS REMOVAL DEVICE

(76) Inventor: Jeffrey Bryan Shapiro, 3301 Stoneridge Dr., Mountain Brook, AL (US) 35223

(*) Notice: Subject to any disclaimer, the term of this patent is extended or adjusted under 35 U.S.C. 154(b) by 114 days.

(21) Appl. No.: 09/655,184

(22) Filed: Sep. 5, 2000

(51) Int. Cl.$^7$ .................................. A61M 1/06
(52) U.S. Cl. ...................... 604/73; 604/35; 604/315
(58) Field of Search .................. 604/319, 35, 37, 604/323, 73, 236, 216, 30, 315; 128/205.19

(56) References Cited

U.S. PATENT DOCUMENTS

| | | | |
|---|---|---|---|
| 4,403,611 A | | 9/1983 | Babbitt et al. |
| 4,995,386 A | * | 2/1991 | Ng ........................ 128/205.19 |
| 4,998,915 A | * | 3/1991 | Hannah ....................... 604/181 |
| 5,098,386 A | | 3/1992 | Smith |
| 5,098,418 A | * | 3/1992 | Maitz et al. ................. 604/141 |
| 5,318,548 A | | 6/1994 | Filshie |
| 5,363,860 A | * | 11/1994 | Nakao et al. ................ 600/573 |
| 5,746,721 A | | 5/1998 | Pasch et al. |
| 5,792,108 A | | 8/1998 | Felix et al. |
| 5,871,278 A | * | 2/1999 | Harry et al. ................. 366/129 |
| 6,135,980 A | * | 10/2000 | Vu .............................. 604/315 |

* cited by examiner

*Primary Examiner*—Dennis Ruhl
*Assistant Examiner*—Linh Truong
(74) *Attorney, Agent, or Firm*—Smith, Gambrell & Rusell, LLP

(57) ABSTRACT

An automatic mucus removal device for extracting mucus from a nasal cavity includes a transportable housing which encases a compact vacuum source connected to a power source, and to which a disposable mucus trap member is removably attached. The housing includes a base portion and a barrel portion, with the mucus trap member preferably attached to one end of the barrel portion. An ejection rod is resiliently mounted to the opposing end of the barrel portion, with the ejection rod operable to expel the mucus trap member from the housing. The user therefore is not required to contact the mucus trap member or the mucus associated with it, and the mucus trap member may be disposed of or cleaned as desired.

19 Claims, 4 Drawing Sheets

AUTOMATIC MUCUS REMOVAL DEVICE

FIELD OF THE INVENTION

The present invention relates to an apparatus which aspirates and removes mucus from nasal and sinus cavities, and, more particularly, to a portable mucus removal device having a disposable mucus trap connected to a continuously operated vacuum to withdraw mucus and other material from nasal and sinus cavities in a hygienic manner.

BACKGROUND OF THE INVENTION

During infancy, most children experience some degree of an allergic condition or upper-respiratory infection that is accompanied by nasal mucus drainage. The degree of nasal mucus drainage varies from slight to chronic depending on the severity of the infection or the allergic reaction. In all cases of infant nasal mucus drainage, however, it is commonly known among pediatric specialists and parents that the best interest of the child is maintained by keeping the child's nasal passages clear of the mucus. Clearing the nasal passages will potentially minimize infectious growth within the sinuses and nasal passages, and some pediatric specialists posit that a more severe upper-respiratory infection may be avoided or minimized if nasal mucus drainage can be promoted during the early stages of a cold or allergic episode. Clearing nasal passages further provides comfort to the child by easing the respiration of the child. Blocked nasal passages make it difficult for children to eat, drink, and, more importantly, sleep during the night.

There are many means through which to help children having nasal mucus drainage. For example, a variety of internally taken drugs are available to control nasal drainage, including prescription and over-the-counter decongestants, nasal drops, and sprays. However, most of these medications for controlling nasal mucus drainage create undesirable side effects when ingested by the child. Additionally, many mechanical devices have been developed that attempt to expel mucus from the nasal passages. However, none of these devices satisfies the hygienic needs of both the user and the child.

One commonly known mucus removing apparatus is a simple hand-operated device that is illustrated in FIG. 1. This simple device consists of a nasal tip 100 attached to a vacuum bulb 102. In operation, the user squeezes the vacuum bulb 102 and then inserts the nasal tip 100 into a nasal cavity of the child. Once the nasal tip 100 is in the nasal cavity, the user releases the vacuum bulb 102, which creates a limited suction in the nasal cavity to draw mucus from the nasal cavity into the nasal tip 100 and vacuum bulb 102. Several problems are encountered by this configuration. First, the suction generated is limited to the volume and strength of the vacuum bulb 102, and therefore the user is required to repeatedly proceed through the cycle of operation to provide adequate suction, which includes the steps of: squeezing the vacuum bulb 102, inserting the nasal tip 100 into the child's nasal cavity, and then releasing the vacuum bulb 102 to create the suction necessary. The user must proceed through this cycle numerous times in order to remove even a small portion of the mucus. This problem is magnified in that most infants do not cooperate with this start-stop technique and will often struggle with the user during the process. Moreover, it is greatly desired that the mucus be discharged from the nasal tip 100 between each cycle of operation of the device. This added step further prolongs the time required to remove the undesired matter, and thus increases potential struggle between the child and the user. Additionally, because the child frequently meets this process with great opposition, the child will usually begin to cry during the struggle, which will correspondingly increase the volume and rate of respiration of the child. This further complicates mucus removal due to the fact that when the mucus is vacuumed close to the nasal opening, the user is required to take the device away to re-squeeze the vacuum bulb 102. During this time, the infant will often inhale vigorously, pulling the mucus from the opening of the nasal passage farther back into the nasal passages, which increases the amount of time taken to complete the task of mucus removal. An additional problem may arise in that the user, depending on the user's hand strength, may experience fatigue during the application of a manual mucus removing device, making the usage of such a device undesirable. Moreover, the user may inadvertently pressurize the vacuum bulb 102 by squeezing the vacuum bulb 102 prematurely prior to removing from the nasal passage, which can push mucus and any other material contained in the device back into the nasal passage instead of removing the mucus.

Another mechanical device that is used to remove mucus is disclosed in U.S. Pat. No. 4,403,611 to Babbitt, et al. The design described in this patent includes a bulky housing which encloses a vacuum, a mucus-collecting compartment, a sterilizing compartment, and a storage compartment. A pair of catheters is attached to the mucus-collecting compartment, such that when the vacuum is operating, the mucus will be pulled through the catheter to the mucus-collecting compartment. The mucus is then contained in the mucus-collecting compartment where it can later be discharged through a coupling connection. The operation of this device presents a series of problems for the user, however. First, while the design provides a means for cleaning the catheter members and for discharging collected mucus by placing them in a cleaning solution in the sterilization compartment, the user must nonetheless physically touch the contaminated area surrounding the catheter members or the coupling connection before cleaning these items. Therefore, this design continues to provide an unclean environment for the user. Additionally, while the design described in the Babbitt patent may be transported by the user, the bulky size of the housing is not easily portable for the user, nor is it easy to use with small children.

A drawback to both of the designs described above, as well as other related embodiments, is that the user is frequently required to touch, at least in some manner, the mucus that was withdrawn by the device. As is commonly known, colds and other infectious pathogens can be spread by a person's contact with nasal mucus that contains the pathogens. Therefore, these devices promote the transfer of colds when the user's hands make contact with the infectious matter and then touch their own various mucus membranes. With the prior art mucus removing devices, there is no mechanism provided to collect and separately contain the removed mucus where it can be disposed of without personal contact. At a minimum, current designs require that the user rinse the infected apparatus in some type of sanitizing solution or boil the entire device to sterilize the system, which means that the user is required to make contact with the device before the device may be sanitized.

What is needed, then, and not found in the prior art, is a device for removing mucus from a person's nasal cavity that provides a consistent suction for eradicating the mucus and that provides a means for disposing of the collected mucus without requiring physical contact by the user.

SUMMARY OF THE INVENTION

An object of the present invention is to provide an apparatus for removing mucus from a person's nasal cavity.

It is a further object of the present invention to provide an apparatus for removing mucus from a person's nasal cavity that provides a substantially steady and consistent suction to remove mucus from a person's nasal cavity.

It is an additional object of the present invention to provide an apparatus for removing mucus from a person's nasal cavity that provides a mucus trap member for collecting the mucus drained via the suction.

It is yet a further object of the present invention to provide an apparatus for removing mucus from a person's nasal cavity that includes ejection means for expelling the mucus trap member away from the housing with minimal, if any, physical contact by the user.

It is yet another object of the present invention to provide an apparatus for removing mucus from a person's nasal cavity that includes a disposable means for collecting the mucus from that person.

It is yet an additional object of the present invention to provide an apparatus for removing mucus from a person's nasal cavity that is portable to easily be used with a small child.

These and other objects of the invention are accomplished through the present automatic mucus removal device for extracting mucus from a nasal cavity. The present invention includes an easily transportable housing which encases a compact vacuum source connected to a power source, and to which a disposable mucus trap member is removably attached. The housing is preferably in the shape of a pistol, having a base portion and a barrel portion. The mucus trap member is preferably attached to one end of the barrel portion of the housing, while an ejection rod is resiliently mounted to the opposing end of the barrel portion. The compact vacuum source and the power source are mounted in the base portion of the housing, with a conduit connecting the vacuum source to the mucus trap member. A switch is further mounted to the housing to provide a switch to provide an electrical connection between the vacuum source and the power source.

In operation, the vacuum source creates a differential pressure that further provides suction within the mucus trap member via the conduit. The mucus trap member is then placed in close proximity to the nasal cavity of the child such that mucus is drawn into the mucus trap member. The mucus is confined in the mucus trap member until the user has substantially extracted the undesirable mucus. Once the project is completed, the user may then depress the ejection rod, which thereby engages the mucus trap member to dislodge the mucus trap member from the housing. The user is therefore not required to contact the mucus trap member or the mucus associated therewith, and the mucus trap member may be discarded or cleaned as desired.

BRIEF DESCRIPTION OF THE DRAWINGS

An automatic mucus removal device embodying the features of the present invention is depicted in the accompanying drawings which form a portion of this disclosure and wherein.

DESCRIPTION OF THE PREFERRED EMBODIMENTS

Figure 1:
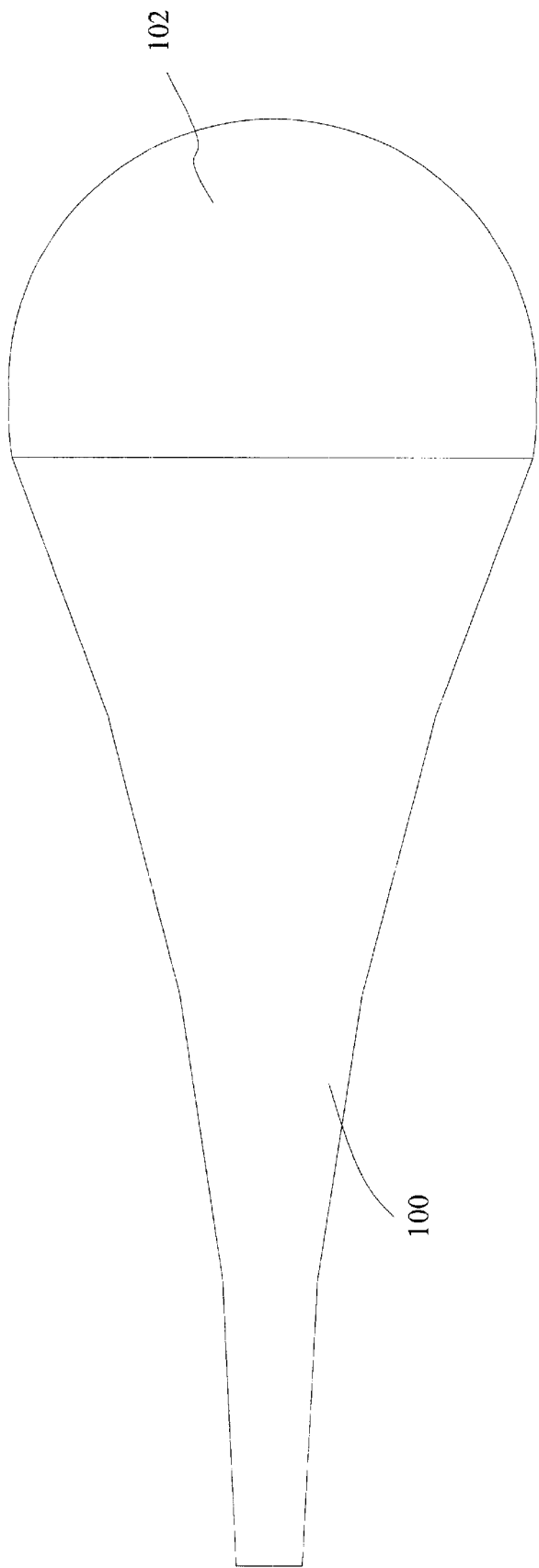
FIG. 1 is a side elevational view of a manually operated mucus removal device of the prior art.
Figure 3:
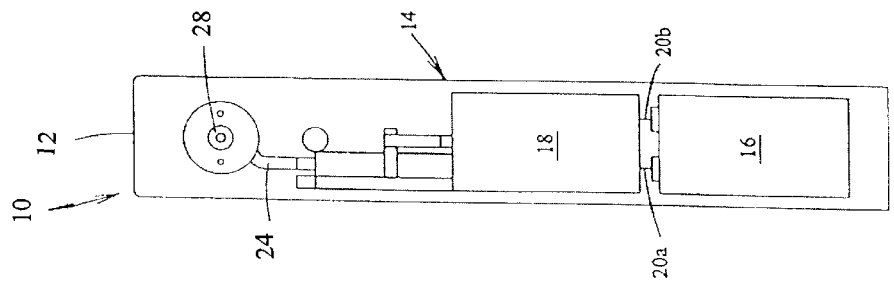
FIG. 3 is a sectional end elevational view of the automatic mucus removal device of the present invention.
Figure 2:
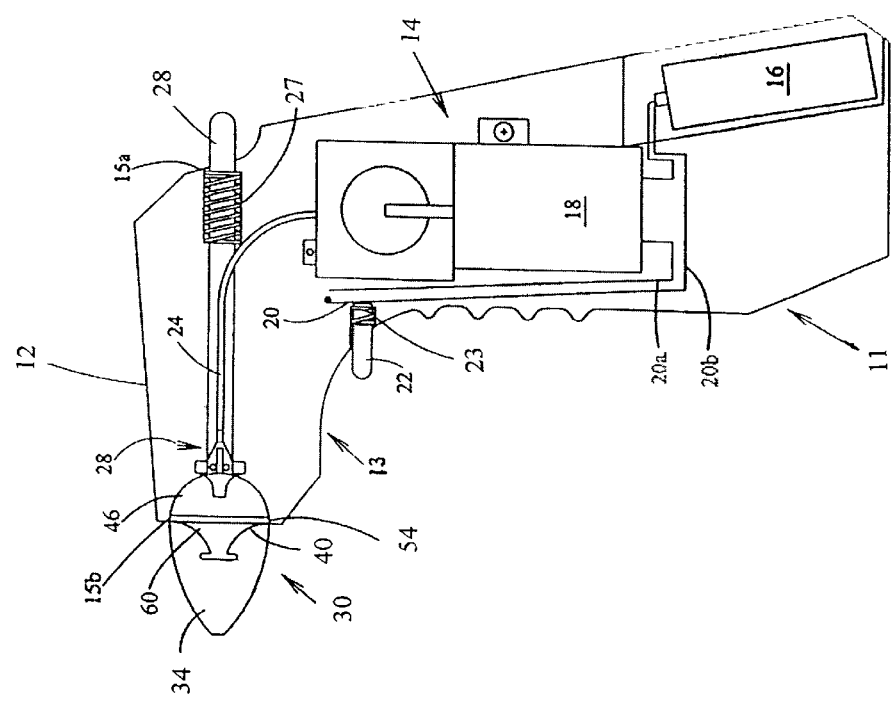
FIG. 2 is a sectional side elevational view of the automatic mucus removal device of the present invention.

Looking at FIGS. 2 and 3, an automatic mucus removal device 10 of the present invention is illustrated. The automatic mucus removal device 10 includes a housing 12 that is preferably in the shape of a conventional pistol, although the housing 12 may be designed to have other shapes as desired by the producer of the housing 12. In the preferred embodiment, the housing 12 has an ergonomically designed base portion 11 (which can easily fit in the palm of an adult hand) and a barrel portion 13. Mounted inside the base portion 11 of the housing 12 is a power means 16, such as a disposable battery, and a vacuum means 14 connected to the power means 16. The automatic mucus removal device 10 further includes an ejection rod 28 that traverses the barrel portion 13 of the housing 12, with a mucus trap member 30 removably affixed to the barrel portion 13 of the housing 12. In addition, the mucus trap member 30 is connected to the vacuum means 14 via a conduit 24.

Continuing to look at FIG. 2, the vacuum means 14 is mounted in the base portion 11 of the housing 12, with the vacuum means 14 including a conventional compact vacuum design known in the art. The vacuum means 14 preferably includes a vacuum motor 18 that is connected to the power means 16. As illustrated, the vacuum motor 18 is also housed within the base portion 11 adjacent the power means 16. The vacuum motor 18 is durable and able to withstand the anticipated stresses and physical shock of common mistreatment of hand held machines, such as drops of the housing 12 from various heights. A series of contact wires 20a, 20b are connected between the vacuum motor 18 and the power means 16 to provide power to the vacuum motor 18 from the power means 16. A switch 22 is additionally connected to the housing 12 to be able to close the electrical circuit between the contact wires 20a, 20b. In the preferred embodiment, the switch 22 is implemented as a trigger that is resiliently mounted, via a conventional spring 23, to the housing 12, preferably at the junction between of the base portion 11 and the barrel portion 13. Other embodiments known in the art for a switch may be implemented as desired. The switch 22 is positioned proximate the contact wires 20a, 20b such that when the user engages the switch 22, the switch 22 will consequently force contact between contact wires 20a, 20b, and close the circuit between the contact wires 20a, 20b. The power means 16 then energizes the vacuum motor 18 to cause the vacuum motor 18 to begin operation. The vacuum means 14 generates a differential pressure that provides a continuous and adequate suction that is safe for use in close proximity of a child (not illustrated) yet will also have sufficient suction to effectively remove mucus from the nasal cavity of the child.

Figure 4:
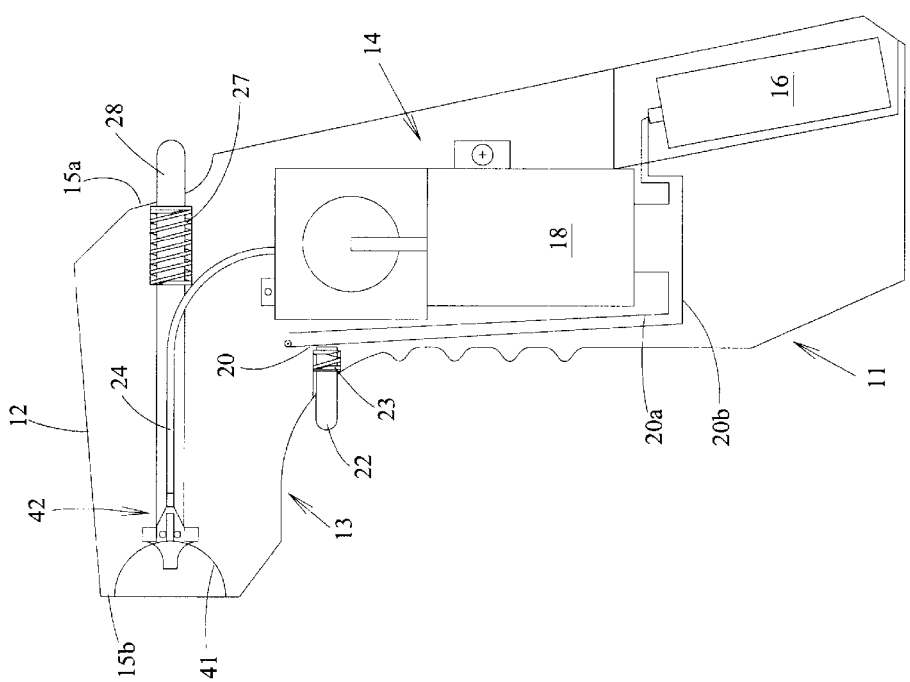
FIG. 4 is a sectional side elevational view of the housing for the automatic mucus removal device as illustrated in FIG. 2, with the mucus trap member removed from the housing.

As stated above, the housing 12 of the automatic mucus removal device 10 includes a barrel portion 13, which has a proximal end 15a and a distal end 15b (see FIG. 2). The mucus trap member 30 is removably attached to the distal end 15b of the barrel portion 13, and the ejection rod 28 is connected to the proximal end 15a of the barrel portion 13. Looking at FIG. 4, the barrel portion 13 defines a recessed cavity 41 at the distal end 15b, with the recessed cavity 41 being a shape that will preferably receive and cradle the mucus trap member 30. A securing means 42 is further included proximate the ejection rod 28, with the securing means 42 being a type known in the art for providing a locking relationship, such as a single latch. The securing means 42 is attached to the housing 12 such that when the mucus trap member 30 is inserted into the recessed cavity 41, the securing means 42 will fasten to the mucus trap member 30. This connection between the securing means 42 and the mucus trap member 30 simply reassures that the mucus trap member 30 will remain in a fixed position with respect to the barrel portion 13 of the housing 12. To further reinforce the connection between the mucus trap member 30 and the housing 12, a gasket 54, such as a conventional O-ring, may be positioned between the base portion 46 and the recessed cavity 41 (see FIG. 2). The gasket 54 will help ensure that there is a snug engagement between the mucus trap member 30 and the recessed cavity 41 of the housing 12.

Figure 5:
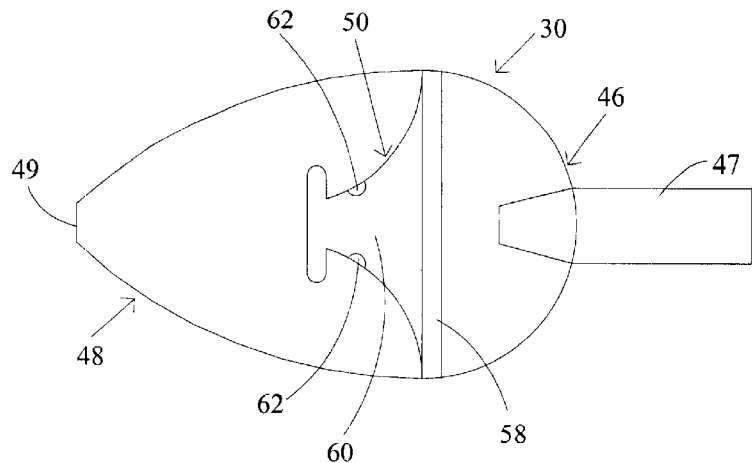
FIG. 5 is a sectional side elevational view of a first embodiment of the mucus trap member of the present invention.
Figure 6:
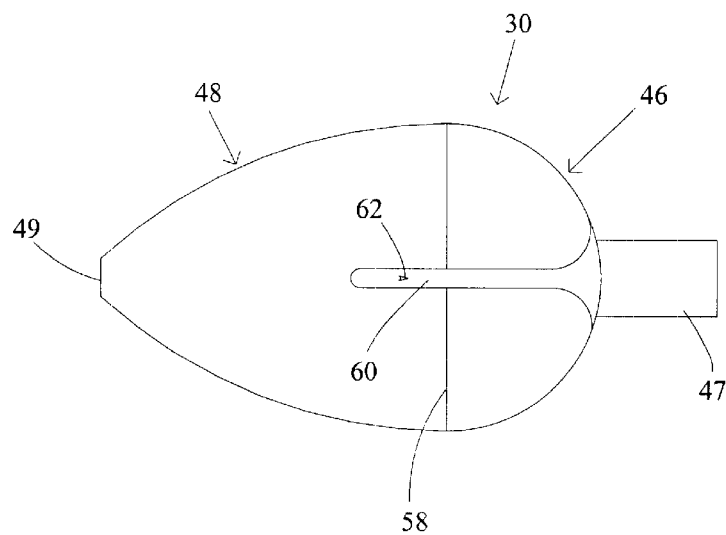
FIG. 6 is a sectional side elevational view of a second embodiment of the mucus trap member of the present invention.

Various embodiments of the mucus trap member 30 are illustrated in FIGS. 5 and 6. In the embodiment illustrated in FIG. 5, the mucus trap member 30 includes three components: a base cup 46, a conical face member 48, and a baffle member 50 firmly positioned between the base cup 46 and the conical face portion 48. However, in the embodiment illustrated in FIG. 6, the mucus trap member 30 includes a base cup 46, a conical face member 48, and a hollow arm 60 connected to the base cup 46. With both embodiments, a vacuum shaft 47 is attached to the base cup 46, with the base cup 46 having a shape similar to that defined by the recessed cavity 41 (illustrated in FIG. 4). The base cup 46 therefore will closely engage the securing means 42 such that the mucus trap member 30 is securely connected to the housing 12. The vacuum shaft 47 will further engage the securing means 42, while the conduit 24 will connect the vacuum means 14 to vacuum shaft 47 to provide suction to the mucus trap member 30.

Looking at FIG. 5, the baffle member 50 includes a plate portion 58 having a hollow arm 60 projecting therefrom. The baffle member 50 is positioned such that the plate portion 58 is locked between the base cup 46 and the conical face portion 48, with the hollow arm 60 projecting away from the plate portion 58 toward the conical face portion 48. In the embodiment illustrated in FIG. 6, the base cup 46 adheres to the conical face portion 48, with the hollow arm 60 projecting from the base cup 46. As stated above, the vacuum means 14 will generate a differential pressure to provide suction in the mucus trap member 30 via the conduit 24. In the embodiment of FIG. 5, the suction is generated within the mucus trap member 30 first in the area surrounded by the base cup 46 and the baffle member 50. At least one baffle aperture 62 is provided in the baffle member 50 (preferably in the end of the hollow arm 60) such that suction is further generated in the area of the mucus trap member 30 surrounded by the conical face portion 58 and the baffle member 50. In the embodiment of FIG. 6, the suction is generated simply within the area surrounded by the base cup 46 and the conical face portion 48 of the mucus trap member 30.

The conical face portion 48 additionally includes a nasal aperture 49, which allows the mucus trap member 30 to provide suction in the external area proximate the nasal aperture 49. Moreover, the diameter of the outer surface of the conical face portion 48 increases from the nasal aperture 49 toward the baffle member 50 to help prevent the unintentional over-insertion of the mucus trap member 30 into a person's nasal cavity. As a result, the user may safely position the nasal aperture 49 adjacent the nasal cavity of the child to remove the mucus. The mucus will then be drawn, through the nasal aperture 49, into the area of the mucus trap member 30 either surrounded by the conical face portion 48 and the baffle member 50 (as in FIG. 5) or in the area surrounded by the base cup 46 and the conical face portion 48. The baffle aperture 62 is located in the hollow arm 60 to limit any mucus from entering the remaining portion of the mucus trap member 30. This location substantially prevents the mucus from being drawn into the conduit 24 or the vacuum means 14. While the baffle aperture 62 is preferably positioned in the middle of the hollow arm 60, it may easily be located at any other point within the mucus trap member 30 so as to provide the desired suction. Moreover, it is to be noted from a comparison of FIGS. 5 and 6 that the shape of the hollow arm 62 may be varied as desired. The central placement of the baffle aperture 62 in the embodiment illustrated in FIG. 6 provides an advantage in that the mucus trap member 30 may be almost half-filled with mucus before there is any concern that the mucus may enter the hollow arm 62.

In the embodiment illustrated in FIG. 5, each of the three components of the mucus trap member 30 (base cup 46, conical face member 48, and baffle member 50) are integrally coupled to each other. Such an arrangement helps to assure that the mucus remains in the mucus trap member 30, and further provides for unproblematic disposal of the mucus trap member 30, and the arrangement further limits the possibility that the mucus within the mucus trap member 30 can be accidentally dispersed into the surrounding environment. However, if desired by the user, an additional embodiment permits the detachable connection of the conical face member 58 with the base cup 56. In such an embodiment, the user may easily clean and re-use the mucus trap member 30 by simply disassembling the three components of the mucus trap member 30 after being used to individually wash the components.

As stated above, the vacuum means 14 is connected to the mucus trap member 30 via the conduit 24, and the vacuum means 14 is able to provide a constant suction in the automatic mucus removal device 10. The conduit 24 is preferably a conventional tube made of plastic or a similar material that is flexible but yet strong enough to withstand the suction generated by the vacuum means 14. One end of the conduit 24 is connected to the vacuum means 14, while the other end of the conduit 24 is connected to the vacuum shaft 47 of the mucus trap member 30.

The operation of the automatic mucus removal device 10 requires the user to hold the base portion 11 of the housing 12 and position the nasal aperture 49 of the mucus trap member 30 proximate the nasal aperture from which mucus is to be removed. The user then engages the switch 22 to activate the vacuum means 14. The vacuum means 14 provides suction through the conduit 24 and mucus trap member 30 to draw mucus into the mucus trap member 30 from the nasal cavity. The mucus is then confined within the mucus trap member 30 until the user either cleans or disposes of the mucus trap member 30. The user can easily dispose of the mucus trap member 30 by engaging the ejection rod 28 to expel the mucus trap member 30 from the barrel portion 13 of the housing 12, such that the user can then easily attach a new sterile mucus trap member 30 to the housing 12.

The arrangement of the securing means 42 in conjunction with the ejection rod 28 provides a means for "hands-free" disposal of the mucus trap member 30 that will effectively eliminate any needed contact by the user with the mucus that is removed from the child. As stated above, the mucus trap member 30 is inserted into the recessed cavity 41 and secured to the housing 12 via the securing means 42. After the user has removed the mucus from the child's nasal cavity into the mucus trap member 30, the user may release the switch 22 and press the end of the ejection rod 28 that extends outward from the proximal end 15a of the barrel portion 13. The ejection rod 28, which is resiliently mounted in the barrel portion 13 via an ejection spring 27, will thereby eject the mucus trap member 30 away from the housing 12 and the securing means 42 without the user having to make physical contact with the mucus trap member 30. The ejection spring 27 will then cause the ejection rod 28 to retract to the original position.

Each mucus trap member 30 is designed such that a sufficient amount of mucus will be stored within the conical face portion 58 of the mucus trap member 30 without having the mucus contaminate the vacuum motor 18. When the desired mucus suction has been completed, the user will simply depress the ejection rod 28 and the mucus trap member 30 away from the housing 12 will simply fall off where it can be disposed of properly without direct contact by the user. A new mucus trap member 30 can then be attached for the next usage of the device.

An additional benefit to the present design over the prior art is that the vacuum means 14 provides a constant suction using differential pressure. As a result, there is no need to remove the mucus removal device 10 from the nasal opening of the child until substantially all of the mucus has been removed from the child's nasal cavity. This allows the user to efficiently clear each nostril in less time, while also minimizing time and the stress within the child during the procedure. This therefore provides a less traumatic experience for both the child and the user. Moreover, the continuous suction provided by the vacuum means 14 of the present invention will remove mucus more effectively than the start/stop method required by prior art manually operated devices. Additionally, the user will not experience hand fatigue as produced by the prior art manually activated devices described above.

A further benefit of the automatic mucus removal device 10 of the present design is that it may be used repeatedly with the user having a minimal risk of coming into contact with the mucus. Therefore, this design is especially advantageous to families with multiple children, and also for child care providers servicing multiple children, in that the self-contained and disposable mucus trap member 30 can be disposed after each usage. As a result, a new, sterile mucus trap member 30 may be attached to the housing 12 to be used with each additional individual child, which improves the speed with which the children can be cleaned and limits the transmittal of infectious germs.

Yet another benefit arises from the fact that the automatic mucus removal device 10 is self-contained, compact in size and the mucus entrapment feature, the automatic mucus removing device 10 can be effectively utilized during travel. If the user has a sufficient amount of the self-contained disposable mucus trap members 30 available, there is no need for the user to have to contact the undesired mucus.

Thus, although there have been described particular embodiments of the present invention of a new and useful AUTOMATIC MUCUS REMOVAL DEVICE, it is not intended that such references be construed as limitations upon the scope of this invention except as set forth in the following claims.

What is claimed is:

1. A mucus removal device comprising:
    a housing;
    a mucus trap member removably attached to said housing, said mucus trap member including a base cup detachably attached to said housing, a tip member attached to said base cup; and a baffle member secured between said base cup and said tip member, said baffle member including a baffle aperture to provide a communication through said baffle member;
    vacuum means for generating a pressure differential, said vacuum means attached to said housing, said vacuum means further connected to said mucus trap member such that said vacuum means provides a pressure differential through said mucus trap member; and
    an ejection member attached to said, housing and engaging said mucus trap member to eject said mucus trap member from said housing.

2. The mucus removal device as described in claim 1 wherein said baffle member comprises a plate portion and a hollow arm, said baffle aperture traversing said hollow arm.

3. The mucus removal device as described in claim 1 wherein said housing comprises:
    a base portion; and
    a barrel portion connected to said base portion, said barrel portion having a proximal end and a distal end;
    wherein said mucus trap member is removably attached to said distal end of said barrel portion.

4. The mucus removal device as described in claim 3 wherein said ejection member is resiliently mounted to said proximal end of said barrel portion extends from said proximal end toward said distal end to engage said mucus trap member.

5. The mucus removal device as described in claim 3 further comprising a recessed cavity to receive said mucus trap member, said recessed cavity defined by said distal end of said barrel portion.

6. The mucus removal device as described in claim 1 further comprising a conduit connecting said vacuum means to said mucus trap member.

7. An apparatus for removing mucus from a nasal cavity of an individual comprising:
    a housing;
    a mucus trap member to engage the nasal cavity of the individual, said mucus trap member attached to said housing and mechanically detachable from said housing;
    an ejection rod mounted to said housing, said ejection rod traversing said housing to engage said mucus trap member to jettison said mucus trap member from said housing without contact by the individual; and
    vacuum means for creating a pressure differential attached to said housing, said vacuum means connected to said mucus trap member to provide the pressure differential through said mucus trap member.

8. The apparatus as described in claim 7 wherein said mucus trap member comprises:
    a base cup removably attached to said housing, said base cup connected to said vacuum means;
    a conical face portion removably attached to said base cup; and
    a baffle member secured between said base cup and said conical face portion, said baffle member including a baffle aperture to allow a communication through said baffle member.

9. The apparatus as described in claim 8 wherein said baffle member comprises a plate portion and a hollow arm, said baffle aperture traversing said hollow arm.

10. The apparatus as described in claim 7 wherein said housing comprises:
   a base portion; and
   a barrel connected to said base portion, said barrel portion having a proximal end and a distal end;
   wherein said mucus trap member is removably attached to said distal end of said barrel portion.

11. The apparatus as described in claim 10 wherein said ejection rod is slidably mounted to said proximal end of said barrel portion, said ejection rod extending from said proximal end toward said distal end to engage said mucus trap member.

12. The apparatus as described in claim 10 further comprising a recessed cavity defined by said distal end of said barrel portion to receive said mucus trap member.

13. The apparatus as described in claim 7 further comprising a conduit connecting said vacuum means to said mucus trap member.

14. The apparatus as described in claim 7 further comprising a gasket positioned between said mucus trap member and said housing.

15. An apparatus for removing mucus from a nasal cavity of a person, the apparatus comprising:
   a housing having a barrel portion and a base portion connected to said barrel portion, said barrel portion having a distal end and a proximal end;
   a mucus trap member removably attached to said distal end of said barrel portion of said housing to engage the nasal cavity;
   an ejection member slidably mounted to said proximal end of said barrel portion of said housing, said ejection member extending from said proximal end toward said distal end to eject said mucus trap member without contact by the person; and
   vacuum means for generating a pressure differential attached to said housing, said vacuum means connected to said mucus trap member via a conduit such that said vacuum means provides a suction through said mucus trap member, wherein the mucus is drawn into said mucus trap member when said mucus trap member is positioned proximate the nasal cavity.

16. The apparatus as described in claim 15 wherein said mucus trap member further comprising:
   a base cup detachably attached to said housing, said base cup connected to said vacuum means;
   a conical face portion attached to said base cup; and
   a baffle member secured between said base cup and said tip member, said baffle including a baffle aperture to provide a communication through said baffle member.

17. The apparatus as described in claim 16 wherein said baffle member comprises a plate portion and a hollow arm, said baffle aperture traversing said hollow arm.

18. The apparatus as described in claim 15 wherein said ejection rod is resiliently mounted to said proximal end of said barrel portion extends from said proximal end toward said distal end to engage said mucus trap member.

19. The apparatus as described in claim 15 further comprising a recessed cavity defined by said distal end of said barrel portion to receive said mucus trap member.

* * * * *